(12) United States Patent
Burgon et al.

(10) Patent No.: US 9,217,692 B2
(45) Date of Patent: Dec. 22, 2015

(54) SAMPLE CLEANING ELEMENT FOR GAS ANALYZER

(71) Applicant: CAMPBELL SCIENTIFIC, INC., Logan, UT (US)

(72) Inventors: Rex P. Burgon, Logan, UT (US); Steven D. Sargent, Logan, UT (US)

(73) Assignee: CAMPBELL SCIENTIFIC, INC., Logan, UT (US)

( * ) Notice: Subject to any disclaimer, the term of this patent is extended or adjusted under 35 U.S.C. 154(b) by 393 days.

(21) Appl. No.: 13/748,365

(22) Filed: Jan. 23, 2013

(65) Prior Publication Data
US 2014/0202234 A1    Jul. 24, 2014

(51) Int. Cl.
*G01N 21/01* (2006.01)
*G01N 1/00* (2006.01)
*G01N 21/15* (2006.01)
*G01N 21/03* (2006.01)
*G01N 33/00* (2006.01)
*B01D 45/12* (2006.01)

(52) U.S. Cl.
CPC ................. *G01N 1/00* (2013.01); *G01N 21/15* (2013.01); *B01D 45/12* (2013.01); *G01N 33/0029* (2013.01); *G01N 2021/0307* (2013.01)

(58) Field of Classification Search
None
See application file for complete search history.

(56) References Cited

U.S. PATENT DOCUMENTS

| | | | |
|---|---|---|---|
| 4,907,166 A * | 3/1990 | Corenman et al. | 702/30 |
| 5,720,650 A * | 2/1998 | Mauze et al. | 451/75 |
| 2003/0015019 A1* | 1/2003 | O'Brien | 73/23.2 |
| 2004/0035183 A1* | 2/2004 | O'Brien et al. | 73/23.36 |
| 2006/0144126 A1* | 7/2006 | O'Brien et al. | 73/23.42 |
| 2008/0041172 A1* | 2/2008 | Jaffe et al. | 73/863.83 |
| 2008/0198381 A1* | 8/2008 | Heggs et al. | 356/437 |

* cited by examiner

*Primary Examiner* — Andre Allen
(74) *Attorney, Agent, or Firm* — Workman Nydegger (57) ABSTRACT

In one example, a sample gas analyzer includes a sample cell configured to receive a gas sample, a sample tube including a passageway that is in communication with the sample cell, and an intake portion. A cleaning element is disposed between, and arranged for fluid communication with, the sample tube and the sample cell, and includes a body having a chamber configured to aid in imparting a rotational motion to a fluid stream entering the chamber. The cleaning element also includes an inlet port that is in communication with the chamber and that is configured and arranged for communication with the atmosphere. Finally, the cleaning element includes an outlet port in communication with the chamber and the sample cell.

17 Claims, 10 Drawing Sheets

SAMPLE CLEANING ELEMENT FOR GAS ANALYZER

BACKGROUND

In order to gather environmental data, scientists and researchers often rely on sensing and analysis systems and devices that can be placed in remote locations and which are able to gather the environmental data with little or no human involvement. Due to the remoteness and/or inaccessibility of their location, such systems and devices may be required to operate reliably for relatively long periods of time without the need for maintenance. One problem experienced with such systems and devices however is that they may become dirty as a result of being exposed to environmental conditions. Some systems and devices may be relatively more susceptible to such problems than other systems and devices.

For example, sensing and analysis systems and devices that use optical elements may be especially sensitive to the presence of dust, dirt, water, and other contaminants. Particularly, such contaminants may adversely affect the accuracy of gathered data and, in the worst case, may prevent operation of the system or device altogether.

BRIEF SUMMARY OF ASPECTS OF SOME EXAMPLE EMBODIMENTS

It should be noted that the embodiments disclosed herein do not constitute an exhaustive summary of all possible embodiments, nor does this brief summary constitute an exhaustive list of all aspects of any particular embodiment(s). Rather, this brief summary simply presents selected aspects of some example embodiments. It should further be noted that nothing herein should be construed as constituting an essential or indispensable element of any invention or embodiment. Rather, various aspects of the disclosed embodiments may be combined in a variety of ways so as to define yet further embodiments. Such further embodiments are considered as being within the scope of this disclosure. As well, none of the embodiments embraced within the scope of this disclosure should be construed as resolving, or being limited to the resolution of, any particular problem(s). Nor should such embodiments be construed to implement, or be limited to implementation of, any particular technical effect(s) or solution(s).

Example embodiments are concerned with sample gas analyzers and related systems and components. Example embodiments within the scope of this disclosure may include, among other things, one or more of the following, in any combination: a sample cell; a pump; a vacuum pump; means for separating a constituent from a flow of gas; means for separating a constituent from a flow of gas by inducing vortex flow in the gas; means for separating a constituent from a flow of gas by inducing a change in direction of the flow of gas; a cleaning element configured to remove one or more of dust and water droplets from a flow of gas; a cyclone separator; a cleaning element; a cleaning element made of one or more of plastic, and metal; a cleaning element that includes a chamber with which one or more inlet ports and an outlet port communicate; a chamber having a generally conical configuration; a chamber having a generally cylindrical configuration; a chamber having a hybrid configuration that includes a cylindrical portion and a conical portion; a cleaning element that includes a chamber and an inlet port configured to communicate with the atmosphere and the chamber; a cleaning element that includes a chamber with which one or more inlet ports and a clean gas outlet port communicate; a cleaning element that includes a chamber with which an inlet port, clean gas outlet port, and dirty gas outlet port communicate; a perforated conduit having a sample inlet at one end and a dirty air outlet at the other; a conduit at least partly disposed within a chamber of a cleaning element; substantially coaxial sample inlet and dirty air outlet; parallel, but non-coaxial, sample inlet and dirty air outlet; a clear air outlet transverse to one or both of a sample inlet and dirty air outlet; a closed path sample gas analyzer; a sonic anemometer; a cleaning element that includes a dirty gas outlet port configured for communication with one or more of a collector, piping downstream of a gas analyzer, and, piping upstream of a vacuum pump; a collector including an inlet connection configured for communication with a cleaning element, and further including an outlet connection; a collector configured for communication with a pump; a sample gas analyzer configured to sample and analyze a gas containing one or more liquids and/or solids; a sample gas analyzer configured to sample and analyze a gas containing one or more of water, water vapor, and carbon dioxide ($CO_2$); and, a sample gas analyzer with a solar-powered component.

BRIEF DESCRIPTION OF THE DRAWINGS

To further clarify at least some of the aspects of embodiments of the present invention, a more particular description of the invention will be rendered by reference to specific embodiments thereof which are illustrated in the appended drawings. It should be appreciated that these drawings depict only typical embodiments of the invention and are therefore not to be considered limiting of its scope. Embodiments of the invention will be described and explained with additional specificity and detail through the use of the accompanying drawings in which:

FIG. 6b is a side view of the example cleaning element of FIG. 6a;

FIG. 6c is a an axial section view of the example cleaning element of FIG. 6a;

FIG. 6d is a radial section view of the example cleaning element of FIG. 6a;

FIG. 7b is a top view of the example cleaning element of FIG. 7a;

FIG. 8b is a side view of the example cleaning element of FIG. 8a;

FIG. 9b is a side view of the example cleaning element of FIG. 9a;

DETAILED DESCRIPTION OF SOME EXAMPLE EMBODIMENTS

At least some example embodiments concern example sample gas analyzers and associated systems and components. Some specific embodiments are concerned with a cleaning element that may be included as part of a sample gas analyzer and/or system.

A. General Aspects of Some Example Cleaning Elements

As embodiments of the cleaning element may be employed in various different environmental conditions, the materials employed in the construction of the cleaning element maybe selected for suitability with such conditions. Some examples of such materials include metals such as steel or aluminum, plastics, rubbers, and combinations of the foregoing. The scope of the invention is not limited to any particular material or combination of materials.

In terms of its size and geometry, embodiments of the cleaning element can be sized and configured as necessary to suit the requirements of a particular application and/or system. However, the scope of the invention is not limited to any particular size or configuration.

With reference to some basic operational characteristics, at least some embodiments of the cleaning element may be configured to induce vortex flow in a sample gas stream. Note that as used herein, "gas" embraces flows and samples that include one or more gases, where such gases may include, for example, carbon dioxide ($CO_2$) and water vapor. The term "gas" also embraces flows and samples of one or more gases that include one or more liquids and/or solids. Such liquids and solids may include, for example, dirt, dust, and liquid water.

Among other things, the vortex flow induced by the cleaning element may cause separation of one or more constituents from the incoming sample gas stream. Separation of such constituents from a gas sample that is to be analyzed may help to maintain the cleanliness of components, such as sample cells for example, for a relatively longer period of time than might otherwise be the case, and thereby reduce the maintenance burden of an associated sample gas analyzer and/or other devices and systems.

In particular, and as noted elsewhere herein, scientists and researchers often rely on sensing and analysis systems and devices that can be placed in remote locations and which are able to gather the environmental data with little or no human involvement. Due to the remoteness and/or inaccessibility of their location, such systems and devices may be required to operate reliably for relatively long periods of time without the need for maintenance. Sensing and analysis systems and devices that use optical elements, for example, may be especially sensitive to the presence of dust, dirt, water, and other contaminants. Particularly, and as discussed in more detail herein, such contaminants may adversely affect the accuracy of gathered data and, in the worst case, may prevent operation of the system or device altogether.

Thus, to the extent that the disclosed cleaning elements can prolong the length of maintenance intervals associated with sensing and analysis systems and devices, such cleaning elements may extend the life of those systems and devices, while also reducing associated maintenance costs. The savings in maintenance costs may be significant, particularly with respect to devices that are located in remote and/or difficult to access locations.

It should be noted that the aforementioned characteristics of a cleaning element are presented solely by way of example and are not intended to limit the scope of the invention in any way.

B. Example Operating Environment

At least some embodiments of the cleaning element may be particularly well-suited for use in devices capable of gathering data concerning the earth and its atmosphere. In one particular example, embodiments of the cleaning element may be employed in connection with devices, such as sample gas analyzers, that rely on a phenomenon/technique that is sometimes referred to as eddy covariance as a basis for collecting data about the movement or transport of materials to and/or from the earth such as water vapor and carbon dioxide, for example. Of course, the eddy covariance phenomenon/technique may be observed and employed in other environments and conditions as well.

In brief, eddy covariance combines fluctuations in vertical wind speed with fluctuations of another atmospheric variable such as carbon dioxide ($CO_2$) concentration, or water vapor concentration, for example. Such fluctuations may be caused by the turbulent mixing of wind. Carbon dioxide and water vapor concentration fluctuations can occur, for example, when swirling winds encounter the water vapor and carbon dioxide. This turbulence may, in turn, greatly enhance $CO_2$ or water vapor flux, or movement of $CO_2$ or water vapor per unit area.

If averaged individually over a period of time, these fluctuations may not be of particular interest since they may indicate no net change in a measured variable. Considered on a combined basis however, the covariance of $CO_2$ or water vapor with vertical wind speed may be of significant interest. Particularly, by mathematically analyzing the changes in these variables, and applying suitable scaling factors, the flux, or movement of water vapor per unit area, of transported water vapor can be determined. Such flux measurements may be helpful in determining, for example, the amount of $CO_2$ or water vapor given off by a particular geographical portion of the earth.

Insofar as the collection of accurate data may rely on the frequency response of the sensing device, that is, the ability of the device to accurately detect fluctuations in one or more variables, mechanisms that adversely affect the frequency response of the sensing device can impair, or even prevent, collection of accurate data. Thus, at least some embodiments of the invention may help to maintain a frequency response of a sensing device within a desired range for a relatively longer period than might otherwise be the case. In some instances, maintenance of the frequency response may be accomplished, at least in part, by components such as a cleaning element which may help to maintain the cleanliness of sensing devices, components, and systems, such as optical sample cells for example.

C. Example Applications

Embodiments of the invention may be useful in any situation or circumstance where it is desired to remove particulates and/or liquid droplets from a gas flow, and may be especially useful where it is desired to eliminate, or reduce the effects of, one or more of the following conditions:

Mixing of a gas stream as it passes through the cleaning element (attenuates fluctuations)

Contact between the cleaned air stream and the material that has been removed (attenuates fluctuations of "sticky" gases)

A high flow rate of the sample gas (can affect the nearby wind velocity measurement)

A relatively high pressure drop in proportion to the flow (increases power consumption and/or affects the performance of the analyzer)

Accumulations of the material removed that degrade performance, either by increasing pressure drop, reducing the effectiveness of the cleaning action, or increased contact between the cleaned air stream and the removed material.

Large size (affects the nearby wind velocity measurement)

Frequent maintenance

High power consumption

Eddy-covariance flux measurement is one example of a situation or circumstance where one or more of the foregoing conditions may be present or is likely to occur. This particular application requires a gas analyzer to measure atmospheric constituents, examples of which include $CO_2$, $H_2O$, $N_2O$, $CH_4$, COS and NH. Some distinguishing characteristics of this particular application are:

It is desired to measure high-frequency fluctuations in the gas of interest.

Attenuation of higher-frequency fluctuations results in an underestimate (bias) of the EC flux.

It is desired to remove particulates and/or liquid droplets that would otherwise contaminate the intake tube and the sample cell and optics of the gas analyzer.

Contamination of the intake tube may affect frequency response, particularly of "sticky" gases such as water vapor or $NH_3$.

Contamination in the gas analyzer may also affect frequency response of sticky gases.

Contamination of the optics or other parts of the analyzer may also affect the performance of the analyzer, by reducing optical transmission, changing the spectral or spatial characteristics of optical transmission, and/or plugging air passages.

Eddy covariance requires the measurement of wind velocity, typically with a sonic anemometer either co-located with, or located near, the air sampling point.

A bulky device near the wind measurement degrades the wind measurement by disturbing the wind flow pattern.

Extracting a high flow rate of air from near the wind measurement position may also adversely affect the wind measurement.

Eddy-covariance measurements are often made at remote locations.

Often there is no access to AC mains power. Low power consumption is desirable to make it easy to power the system from solar panels and batteries, or other types of remote power, examples of which include wind generators, fuel cells, and conventional generators.

Remote sites make on-site maintenance time-consuming and expensive.

As disclosed herein, embodiments of the invention may be effective in reducing the impact of, or even eliminating, the occurrence of one or more of the aforementioned conditions.

D. Example Analyzer and System Embodiments

Prior to a detailed discussion of the Figures, some general information is presented concerning the example embodiments disclosed in those Figures. Among other things, the following embodiments may: decrease maintenance, minimize pressure drop at a given flow rate to minimize the power consumption for the pump that moves the gas sample through the cleaning element, minimize physical size to allow placement of the cleaning element next to a wind measurement with minimal flow disturbance, and/or minimize interaction of the gas stream with material that has been removed to preserve fluctuations in sticky constituents such as water vapor.

In general, and as indicated by the examples in the table below, there are a variety of possible configurations of a cleaning element.

| Config # | # of ports | Port Layout | Flow | FIG. | In | Clean out | Dirty Out | Dust Coll. | Notes |
|---|---|---|---|---|---|---|---|---|---|
| 1 | 3 | T | Vortex | 6 | 402 | 404 | 406 | No | |
| 2 | 2 | T | Vortex | 6 | 402 | 404 | None | Yes | Dirt accumulates in point of cone |
| 3 | 3 | T | Straight | 6 | 404 | 402 | 406 | No | Same as #1, but reverse flow direction |
| 4 | 2 | T | Straight | 6 | 404 | 402 | None | Yes | Same as #2, but reverse flow direction |
| 5 | 3 | F | Vortex | 7 | 508 | 514 | 510 | Yes | Similar to #1, but both outlets in same end |
| 6 | 2 | F | Vortex | 7 | 508 | 514 | none | Yes | Same as #5, but no dirty outlet |
| 7 | 3 | T | Vortex | 8 | 604 | 610 | 606 | No | Same as #1 but no conical section, only cylindrical |
| 8 | 2 | T | Vortex | na | 604 | 610 | none | Yes | Same as #7 but no dirty outlet flow. Dirt accumulates in end of cylinder. |
| 9 | 3 | Coax | Straight | 9 | 704 | 710 | 708 | No | Dirty flow into a continuous, perforated tube. Clean air extracted transversely, dirty air outlet in straight line. |

Figure 1:
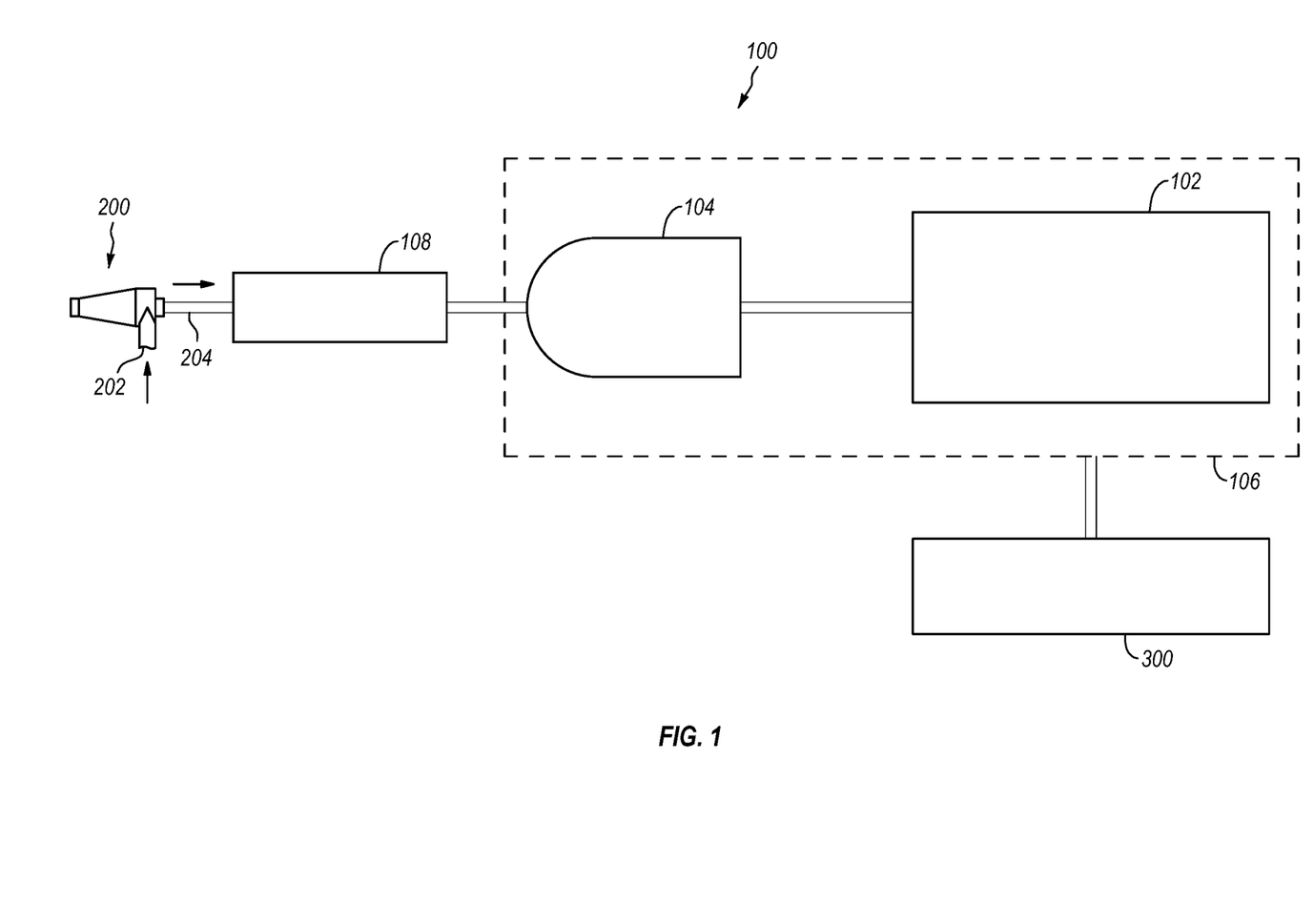
FIG. 1 discloses aspects of an example sample gas analyzer system that includes a two port cleaning element.

Directing attention now to FIG. 1, details are provided concerning an example of a system 100 in which a cleaning element 200 may be employed. In one example embodiment, the system 100 comprises a closed-path sample gas analyzer, one example of which is the EC155 Closed-Path $CO_2/H_2O$ Gas Analyzer, produced by Campbell Scientific. Further details concerning the EC155 are disclosed in the documents located at http://s.campbellsci.com/documents/us/product-brochures/b_ec155.pdf, and at http://s.campbellsci.com/documents/us/manuals/ec155.pdf, both of which documents are incorporated herein in their respective entireties by this reference. As disclosed elsewhere herein, a closed-path sample gas analyzer, of which the EC155 is but one example, may be combined with other elements such as a pump and/or data logger.

In the example of FIG. 1, the system 100 may include a pump 102, such as a vacuum pump for example, that is arranged for communication with a sample cell 104. One or more components of the system 100, such as the pump 102 for example, may be solar-powered, although other power sources may alternatively be employed. The sample cell 104 may or may not comprise an optical sample cell. As indicated in FIG. 1, one or more components of the system 100 may be contained within a housing 106, although such an arrangement is not necessary. The housing 106 may be configured to substantially prevent the ingress of foreign matter, such as water and/or dust for example, that could contaminate components inside the housing 106. As well, the housing 106 may include power, and other, connections for components contained in the housing 106.

Returning now to FIG. 1, the sample cell 104 is arranged for communication with a sample tube 108. Finally, and as noted above, a cleaning element 200 is provided that is arranged for communication with the sample tube 108. In some embodiments, multiple cleaning elements 200 may be provided. In such embodiments, the cleaning elements 200 may be arranged in series so that, for example, the clean gas outlet of one of the cleaning elements 200 is connected with the inlet port 202 of a downstream cleaning element. In such arrangements, a cleaning element 200 may be combined with another cleaning element that may or may not be identical to the cleaning element 200. As well, due consideration must be given to design parameters, such as flow rate and pressure drop for example, to ensure that desired performance of a system 100 that employs multiple cleaning elements 200 is maintained.

In the example of FIG. 1, the cleaning element includes an inlet port 202 by way of which a gas sample enters the cleaning element 200. The inlet port 202 may or may not include a strainer, screen, filter or similar device to prevent the ingress of contaminants. As well, the example cleaning element 200 further includes a clean gas outlet 204 that communicates with the sample tube 108.

In operation, and with reference to the example of FIG. 1, the pump 102 operates to draw a gas sample, such as atmospheric air for example, into the cleaning element 200 by way of the inlet port 202. A cleaning operation performed by the cleaning element 200, discussed in more detail below, produces a flow of clean gas, or at least gas that is relatively cleaner than the sample that entered through inlet port 202. Materials removed from the sample may be collected in the cleaning element 200 and retained there for subsequent removal. The clean gas then exits the cleaning element 200 through the clean gas outlet 204, and enters the sample tube 108 from which the clean gas is then conveyed to the sample cell 104 where the clean gas can then be analyzed. After passing through the pump 102, the sample gas may be exhausted to the atmosphere or may be conveyed to the inlet of a second gas analyzer system.

In at least some instances, embodiments such as system 100 may be employed in connection with a data logger 300 that may or may not be configured for wireless communication with a data reception location. Thus, the data logger 300 may collect and store the analytical data produced by the sample cell 104. The data logger 300 may store these data until they are retrieved by during a maintenance visit, or it may or may not then transmit that data on a periodic, or other, basis to a data reception location remote from the location where the system 100 is located. The data logger 300 may or may not be solar-powered. The data logger 300 may or may not be at the same location as the system 100. As well, the data logger 300 may or may not be disposed within the housing 106.

Figure 2:
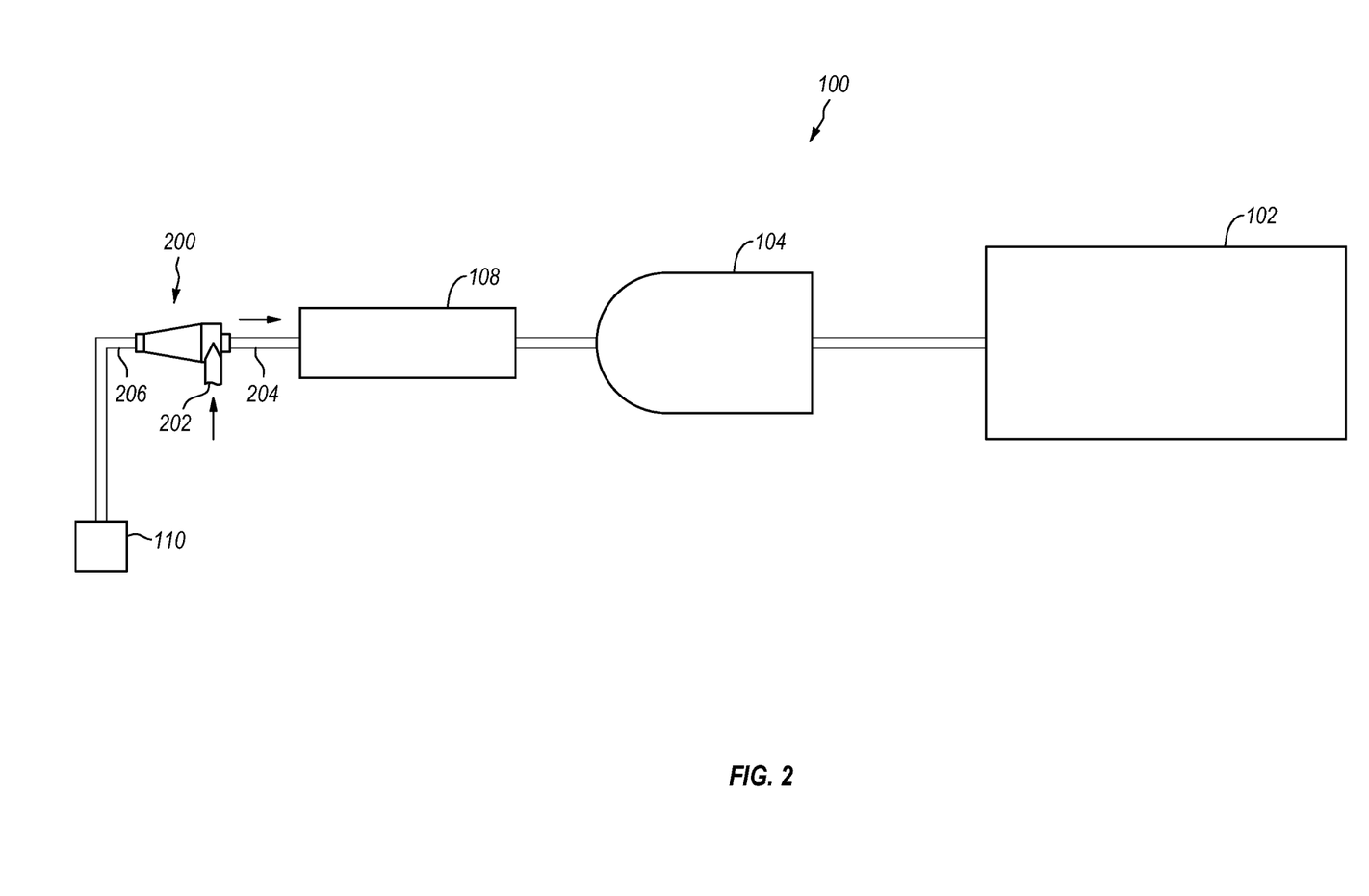
FIG. 2 discloses aspects of an example sample gas analyzer system that includes a cleaning element having a port in communication with a collector.

Turning now to FIG. 2, another example system 100 is disclosed. Except as noted below, the example system 100 disclosed in FIG. 2 may be similar, or identical, to the example system 100 disclosed in FIG. 1.

In the example of FIG. 2, the cleaning element 200 may include a dirty gas outlet 206 by way of which materials, such as dirt, dust, and water drops for example, removed from the gas sample received by way of inlet port 202 can be directed out of the cleaning element 200. Additionally, a collector 110 may be provided that is connected to the dirty gas outlet 206 and configured to receive and retain materials removed from the incoming gas sample. In the example of FIG. 2, the collector 110 serves as a dead end for the dirty gas outlet 206, inasmuch as the collector 110 is not connected to any other part of the system 100.

The collector 110 may include a removable element, such as a basket for example, that captures and retains such materials for later disposal. The removable element may or may not be reusable. Finally, the collector 110 may be implemented as, or comprise, a trap, filter, or any other device(s) configured to capture and retain materials separated from the incoming gas flow.

Figure 3:
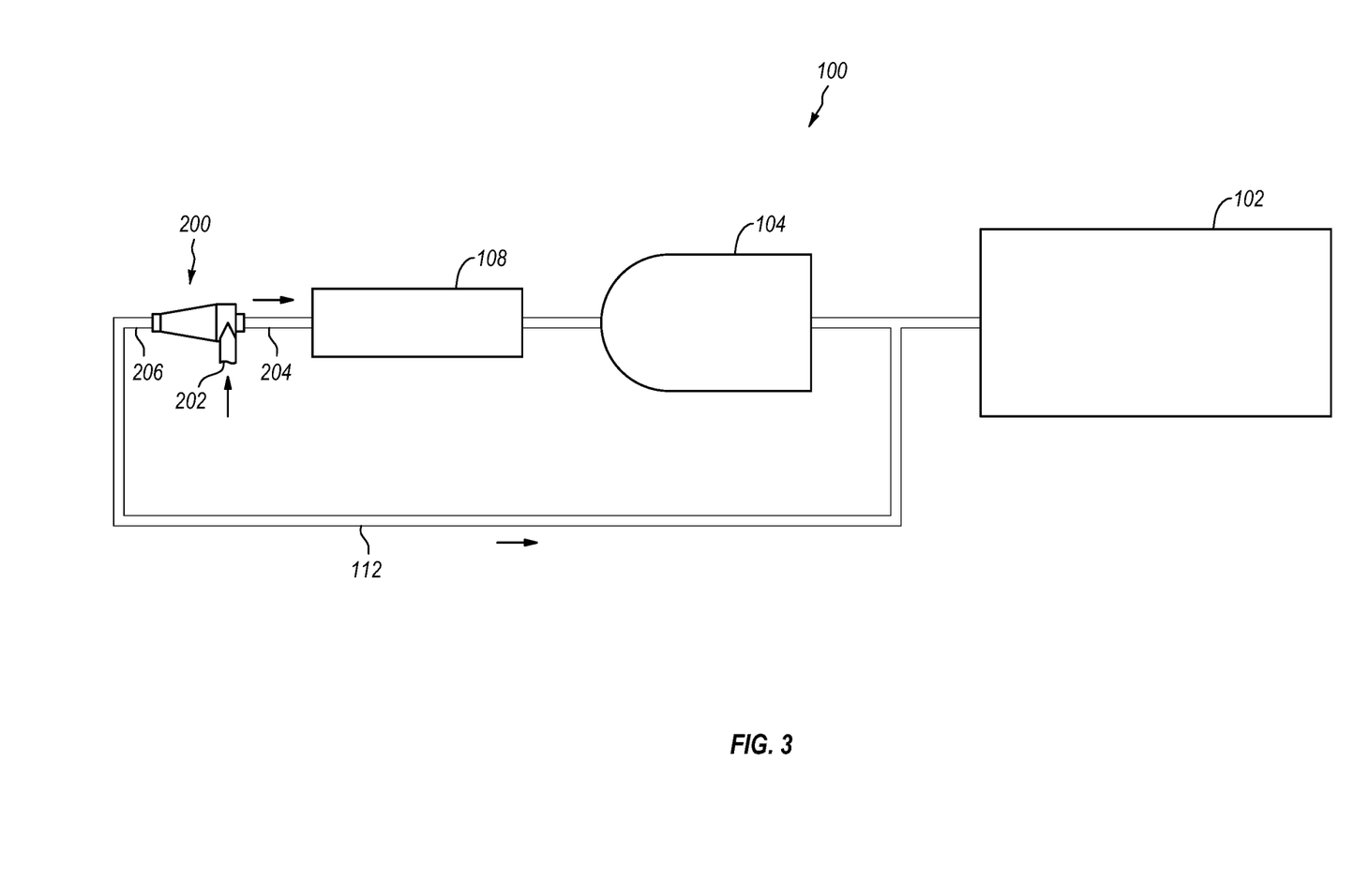
FIG. 3 discloses aspects of an example sample gas analyzer system that includes a cleaning element having a dirty gas outlet port connected to a dirty gas return line that feeds back into a portion of the sample gas analyzer system.

With reference now to FIG. 3, another example system 100 is disclosed. Except as noted below, the example system 100 disclosed in FIG. 3 may be similar, or identical, to the example system 100 disclosed in FIG. 2.

In the example of FIG. 3, the dirty gas outlet 206 of the cleaning element 200 may be connected to a dirty gas return line 112 that connects to another part of the system 100. In one example, the dirty gas return line 112 is connected to the system 100 downstream of the sample cell 104 and upstream of the pump 102. In this way, the dirty gas return line 112 bypasses the sample cell 104 and, among other things, such an arrangement may permit use of the pump 102 to draw separated materials away from the cleaning element 200.

Figure 4:
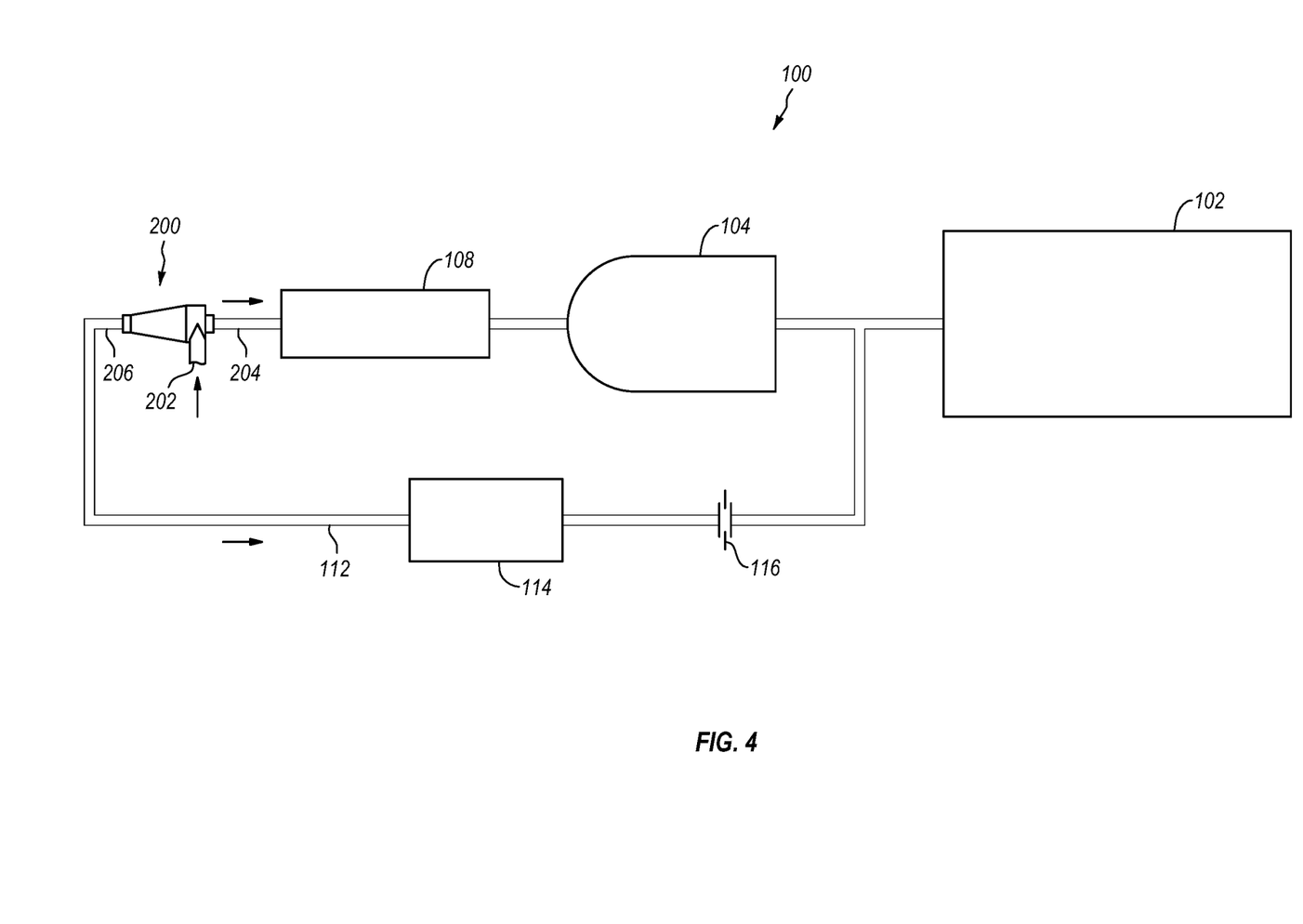
FIG. 4 discloses aspects of an example sample gas analyzer system that includes a cleaning element having a dirty gas outlet port connected to a dirty gas return line that feeds back into a portion of the sample gas analyzer system, the dirty gas return line including one or more collectors and/or cleaning elements.

In some instances, and with reference now to FIG. 4, the dirty gas return line 112 may include one or more elements 114. The element 114 may comprise one or more of an in-line collector, filter, or another cleaning element such as cleaning element 200. In at least one example, one of the aforementioned devices may be configured to be blown out, or cleaned, by reversing the flow of the pump 102. The device may include a connection to the atmosphere to enable trapped materials in the device to be expelled during the blow out process. In this particular example, a check valve or comparable device may be provided in the dirty gas return line 112 between such a device and the cleaning element 200 so that separated materials in the device do not flow back to the cleaning element 200.

As well, the dirty gas return line 112 may include one or more flow restrictors 116, such as an orifice, or other device(s) of comparable functionality to provide a desired pressure drop relative to that provided by the combination of the cleaning element 200, sample tube 108, and sample cell 104. It may be desirable in at least some instances to select the flow restrictor or other devices such that the flow rate through the dirty gas return line is relatively lower, possibly substantially lower in some instances, than the flow rate through the sample cell 104.

It should be noted that any one or more of the aforementioned variations in the dirty gas return line 112 may be combined together in any desired combination, and the scope of the invention is not limited to the examples noted above.

Figure 5A:
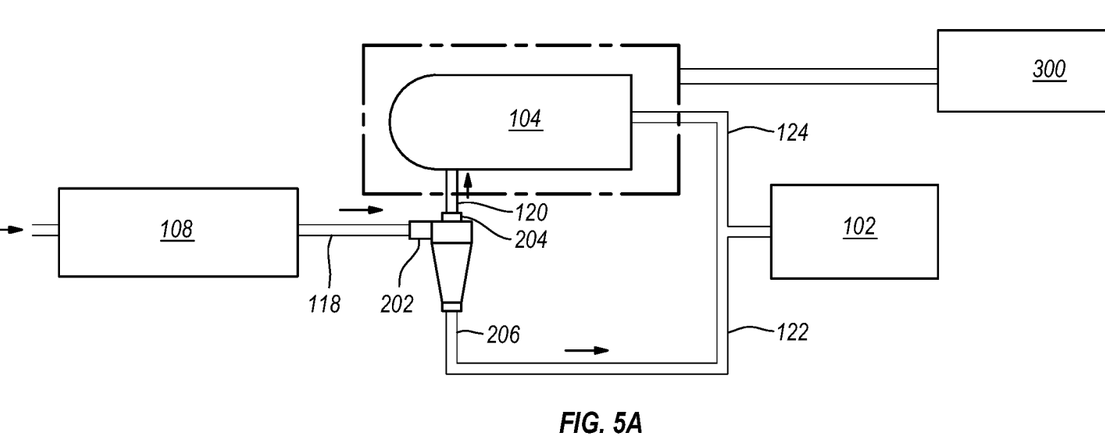
FIG. 5a discloses aspects of an example gas analyzer system having a pump and data logger disposed in separate housings.
Figure 5B:
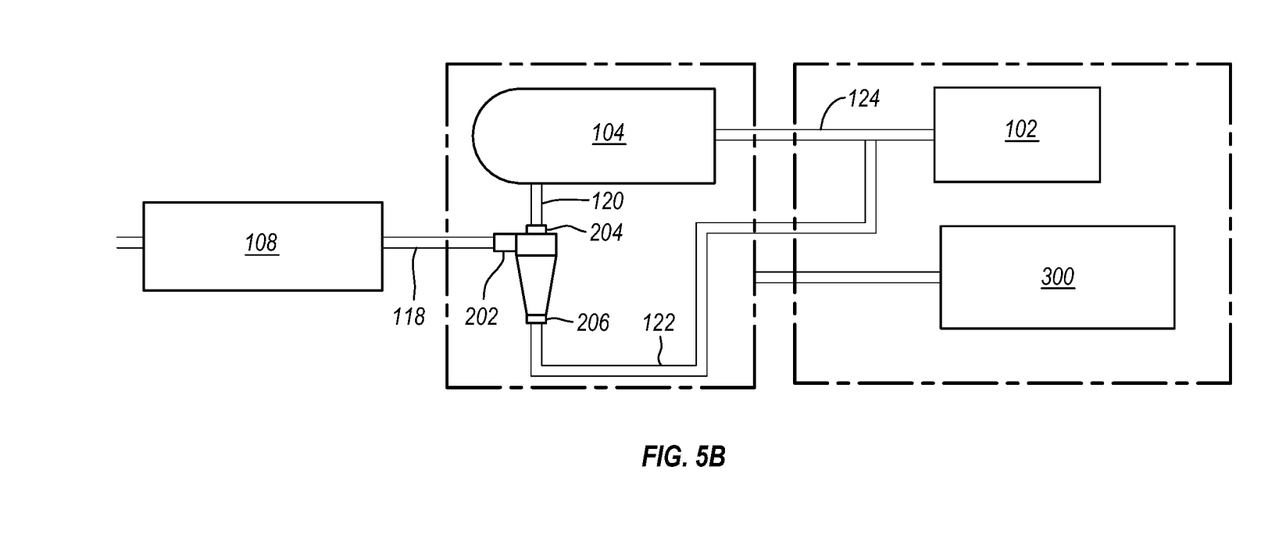
FIG. 5b discloses aspects of an example gas analyzers system having a pump and data logger disposed together in a single housing.

With attention now to FIGS. 5a and 5b, further aspects of some example embodiments are disclosed. In the example of FIG. 5a, the pump 102 and data logger 300 are disposed in separate respective housings. As well, and in contrast with the example embodiment of FIG. 1, the sample tube 108 is located upstream of the cleaning element 200 such that a gas sample drawn into the sample tube 108 exits the sample tube 108, passes through the sample tube outlet line 118, and enters the cleaning element 200 by way of the inlet port 202. The clean sample gas then exits the cleaning element 200 by way of the clean gas outlet 204, passes through the clean gas outlet line 120 and enters the sample cell 104. As well, exhaust from the cleaning element 200 exits by way of the dirty gas outlet 206, and passes through the dirty gas return line 122 which is connected to the inlet of the pump 102. The sample cell outlet line 124 of the sample cell 104 is likewise connected to the inlet of the pump 102. Where, as in the arrangement of FIG. 5a, the sample cell 104 outlet and the cleaning element 200 dirty gas outlet 206 share a common connection with the pump 102, a backflow preventer (not shown), such as a check valve for example, may be placed in the outlet of the sample cell 104 and the dirty gas line of the cleaning element 200.

Turning now to FIG. 5b, the example embodiment disclosed there is the same as the embodiment of FIG. 5a in terms of the connections of the various elements to each other. However, the embodiment of FIG. 5b differs from that of FIG. 5a in that the pump 102 and data logger 300 are combined together in a single housing. The embodiments of FIGS. 5a and 5b also differ in that in the embodiment of FIG. 5b, the sample cell 104 and cleaning element 200 are combined together in a single housing while, in the embodiment of FIG. 5a, the sample cell 104 and cleaning element 200 are separate from each other.

More generally however, the various components disclosed in FIGS. 1-4, 5a and 5b, can be combined together in any suitable way, and the scope of the invention is not limited to those example configurations set forth in the Figures.

E. Structural Aspects of Example Embodiments of a Cleaning Element

With reference now to FIGS. 6a-6d, details are provided concerning an example embodiment of a cleaning element, denoted at 400, one example of which is a cyclone separator. In particular embodiment of FIGS. 6a-6d, the cleaning element 400 includes an inlet port 402, clean gas outlet port 404, and dirty gas outlet port 406. Each of the inlet port 402, clean gas outlet port 404, and dirty gas outlet port 406 may be configured to communicate with a chamber 408 defined by the body 410 of the cleaning element 400. Some embodiments of the cleaning element 400 may omit the dirty gas outlet port 406. As well, some embodiments may include multiple chambers arranged in series or in parallel with each other. One of such chambers may serve as a collector for separated materials. Some embodiments may include multiple inlet ports, clean gas outlet ports, or dirty gas outlet ports.

Further, while some embodiments of a cleaning element are in the form of elements separate from other components of a system, such as system 100 for example, in other instances, some or all portions of a cleaning element may be integrated together with one or more other components of a system. By way of illustration, in at least one embodiment, the cleaning element may be integrally formed as part of the sample cell. For example, some or all of the elements of the cleaning element could be machined into the same block of material as the sample cell.

Figure 6A:
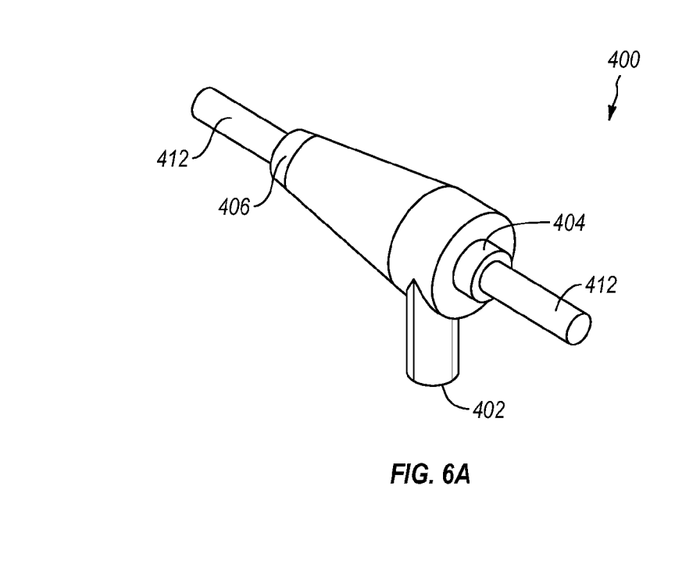
FIG. 6a is a perspective view of an example cleaning element.
Figure 6B:
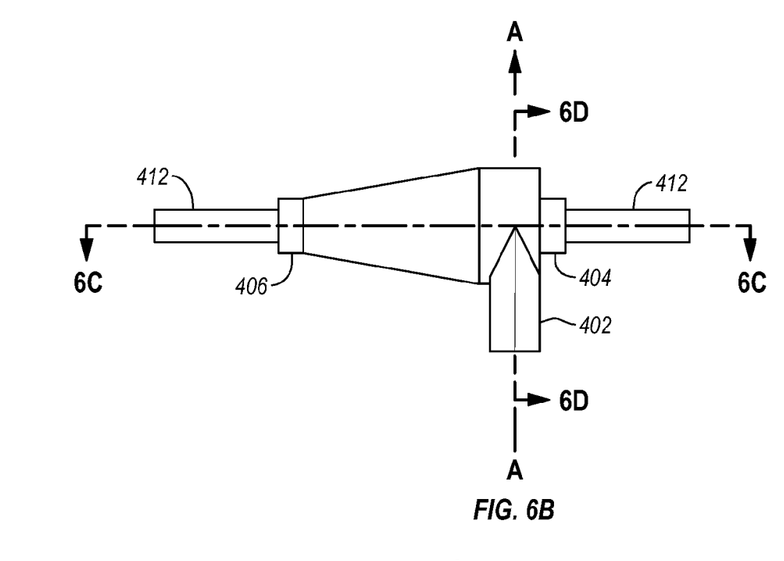
Figure 6C:
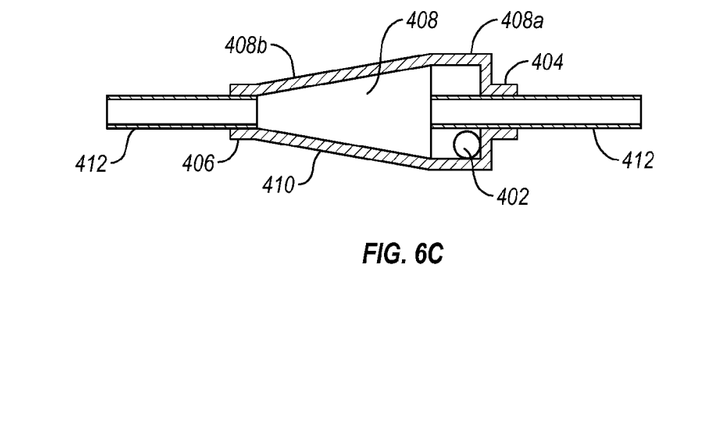

With particular reference to the chamber 408 and the example of FIG. 6c, the chamber 408 may be tapered, so as to form a substantially conical configuration for example, such that the diameter of the chamber 408 at the first end 408a is greater than the diameter of the chamber 408 at the second end 408b. In one particular embodiment indicated in FIG. 6c, the body 410 may define a chamber 408 that includes a substantially conical portion that is abutted by a substantially cylindrical portion at one or both ends of the substantially conical portion, although this configuration is not necessary.

In some, though not all, embodiments, a portion or all of embodiments of a body, such as the body 410, may be formed from a piece of tubing. Some or all portions embodiments of the body of a cleaning element may alternatively be cast, machined, milled, injection molded, or otherwise formed. In some instances, the body may comprise two portions removably attached to each other, such as by way of threads or other mechanisms. Such a configuration may permit access to a chamber inside the body so as to empty the chamber of collected materials and/or modify, repair, or replace components disposed within the chamber.

Of course, one or more aspects of the geometry of the chamber 408 and body 410 may be varied as necessary to suit the anticipated application(s) of the cleaning element 400. Accordingly, the embodiment of FIGS. 6a-6d is presented by way of example only, with the understanding that other shapes, sizes, and configurations of the chamber 408 and/or body 410 may alternatively be employed.

As best disclosed in FIG. 6c, the body 410 and chamber 408 may be configured so that tubing 412 can be inserted into clean gas outlet port 404 and/or dirty gas outlet port 406 to a point near the abutment of the substantially cylindrical and substantially conical portions of the chamber 408, although in other embodiments, the body 410 and chamber 408 may be configured so that tubing 412 can be inserted into the chamber 408 to a greater, or lesser, extent. In some instances, one or more stops or similar elements may be included as part of the body 410 so as to limit the extent to which tubing can be inserted into the chamber 408. Where it is desired to be able to vary the extent to which tubing can be inserted into the chamber 408, a port and corresponding tubing may include threads or other elements that enable changes to the position of the tubing relative to the port.

As noted above, and with continued reference to FIGS. 6a-6d, various ports may be provided in the cleaning element 400. In terms of an example configuration, the inlet port 402 and the clean gas outlet port 404 may be located proximate a first end 408a of the chamber 408, while the dirty gas outlet port 406 may be located proximate a second end 408b of the chamber 408. The inlet port 402, which may be exposed to the atmosphere in some embodiments, may have a flared, tapered, or bell-shaped configuration to help prevent the ingress of water from condensation, rain, or other precipitation. The inlet port 402 may have a screen or other device(s) of comparable functionality to help prevent the ingress of foreign materials such as dust, pollen or other plant materials, insects, spiders, or spider webs.

Figure 6D:
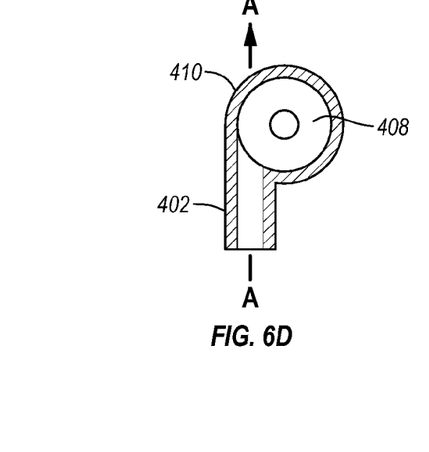
Figure 7A:
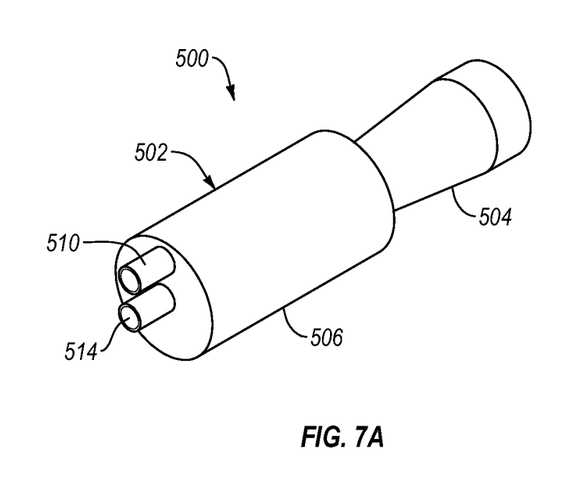
FIG. 7a is a perspective view of another example cleaning element.
Figure 7B:
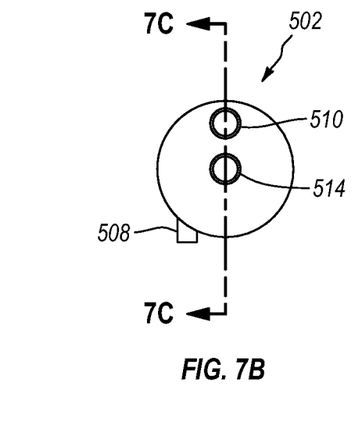
Figure 7C:
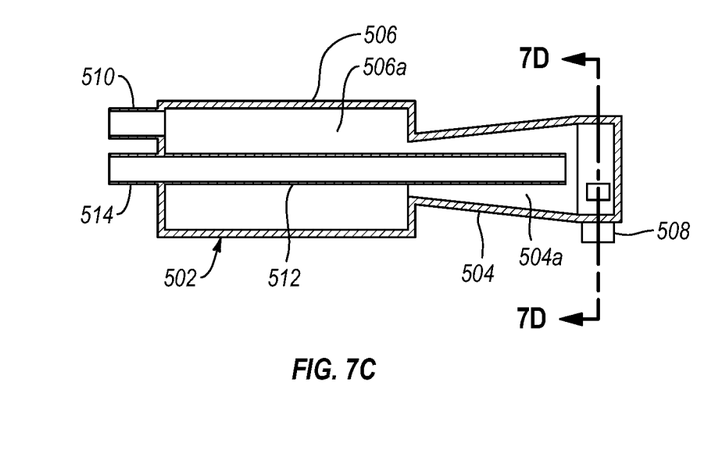
FIG. 7c is a section view taken from FIG. 7b.
Figure 7D:
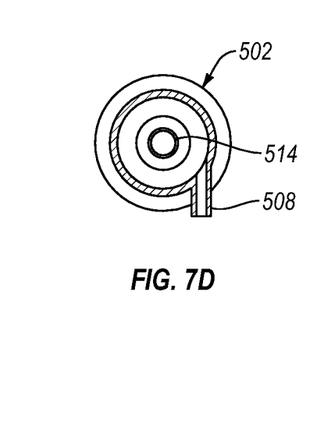
FIG. 7d is a section view taken from FIG. 7c.
Figure 8A:
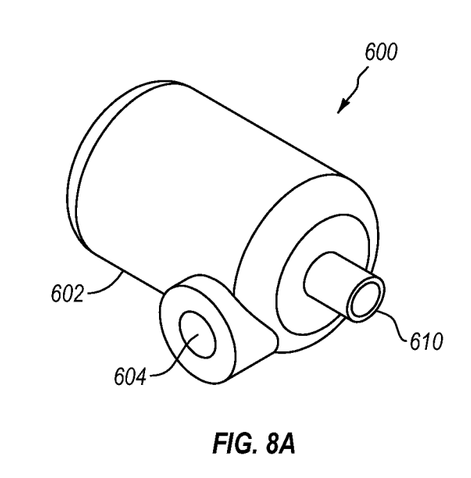
FIG. 8a is a perspective view of another example cleaning element.
Figure 8B:
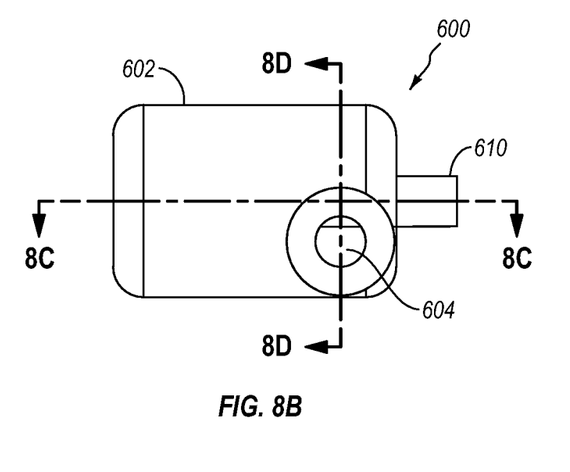
Figure 8C:
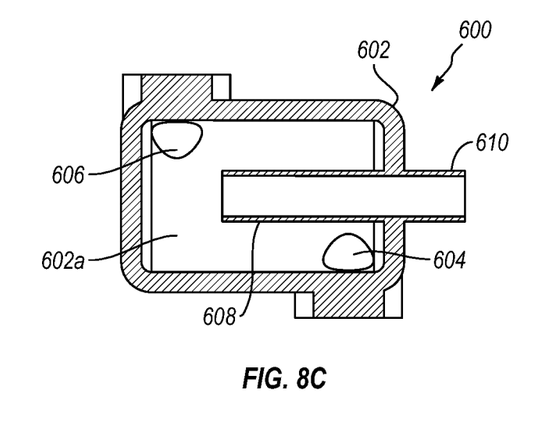
FIG. 8c is a section view taken from FIG. 8b.
Figure 8D:
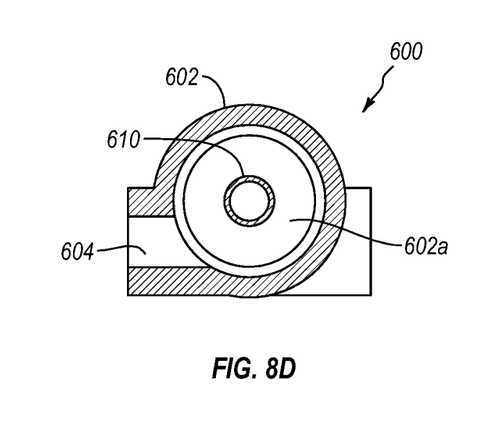
FIG. 8d is a section view taken from FIG. 8b.
Figure 9A:
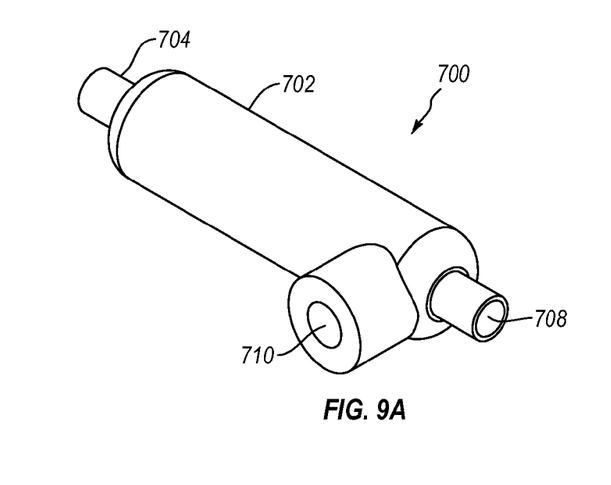
FIG. 9a is a perspective view of another example cleaning element.
Figure 9B:
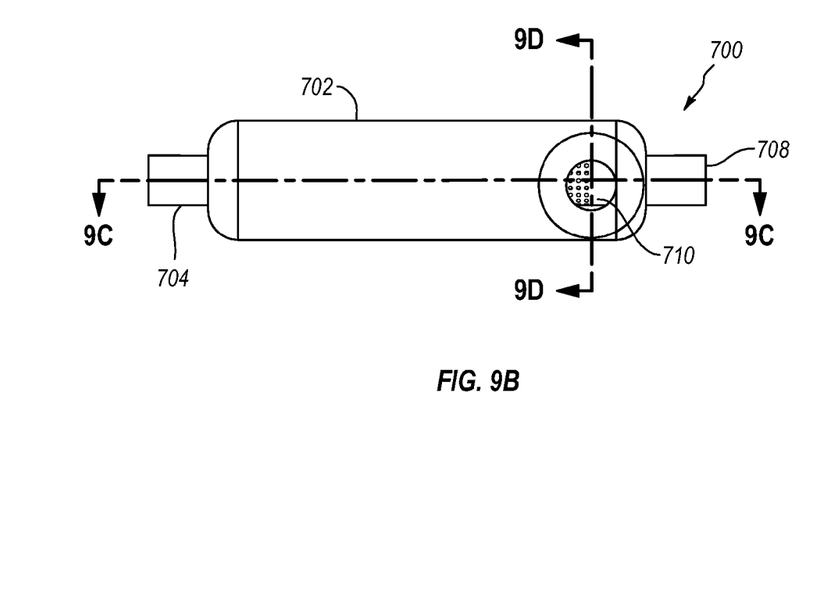
Figure 9C:
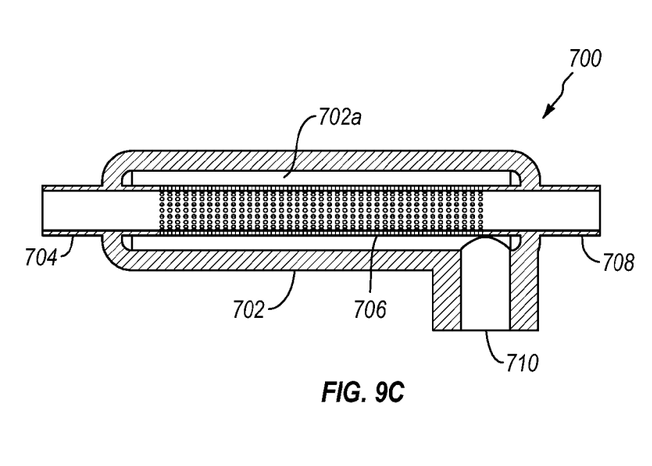
FIG. 9c is a section view taken from FIG. 9b.
Figure 9D:
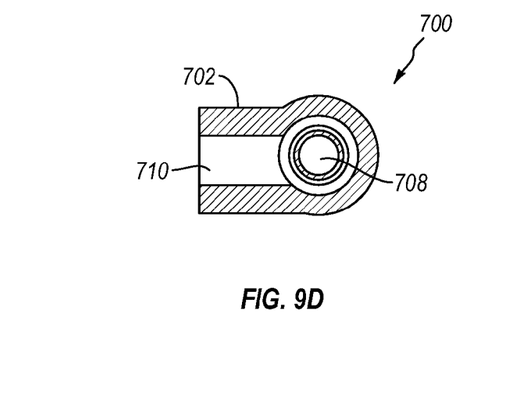
FIG. 9d is a section view taken from FIG. 9b.

More specifically, and as indicated in FIG. 6d, the inlet port 402 may define a longitudinal axis A-A that may be oriented substantially tangentially to a portion of the chamber 408. As disclosed in more detail elsewhere herein, this arrangement may be useful in achieving separation of materials from a flow of gas entering inlet port 402. As best disclosed in FIGS. 6b and 6c, one or more of the clean gas outlet port 404, chamber 408, and dirty gas outlet 406 may be substantially coaxial with each other, and/or substantially perpendicular to axis A-A defined by the inlet port 402, although such an arrangement is not necessary. Inlet port 402 may intersect chamber 408 at some other non-perpendicular angle so as to impart momentum to the gas entering chamber 408 with a direction that optimizes performance.

Directing continued attention to FIGS. 6a-6d, embodiments of the cleaning element 400 may be configured so that one or more of the inlet port 402, the clean gas outlet port 404, and the dirty gas outlet port 406 comprise a socket connection configured to receive tubing 412 which may be glued, brazed, welded, or friction fit, for example, into a port. As another example, one or more of the ports may be molded onto corresponding pieces of tubing. Alternatively, one or more of the socket connections may comprise a compression fitting, or a threaded fitting. The tubing 412 may be copper, steel, or any other metal(s), plastic or other non-metallic material. One or more of the inlet port 402, the clean gas outlet port 404, and the dirty gas outlet port 406 may or may not be the same size as one or more of the other of the inlet port 402, clean gas outlet port 404, and dirty gas outlet port 406. If desired, one or more of the aforementioned ports may include an O-ring or other sealing member(s).

With regard now to some more general aspects of example embodiments of the cleaning element 400, some or all of the interior surface of the chamber 408 may be treated, textured, coated or finished in such a way as to aid in achievement of a desired effect, such as, for example, enhanced separation of materials from an incoming flow of gas. For example, some or all portions of the interior surface of the chamber 408 may be relatively rough, relatively smooth, or a combination of the two.

As well, the body 410 of the cleaning element 400 may be cast, machined, milled, shaped, formed, injection-molded, or constructed using any other suitable process(es), and the body 410 may be implemented as a unitary one-piece construction or, alternatively, may comprise an assembly of two or more discrete parts. The body 410 may have any suitable length. In one example embodiment, the body 410 defines a chamber 408 whose sides cooperate to define an angle in a range of about 15 degrees to about 25 degrees, such as 20 degrees for example. However, greater or smaller angles may alternatively be employed.

Turning now to FIGS. 7a-7d, details are provided concerning another embodiment of a cleaning element, denoted at 500. The materials employed in the construction of the cleaning element 500 may be similar or identical to those used in the other embodiments disclosed herein. As well, the cleaning element 500 may be employed in any system, such as system 100 for example, that utilizes a cleaning element having a three port configuration. Examples of such systems are disclosed in FIGS. 1-4 and 5a-5b.

In general, the cleaning element 500 may include a body 502 having first and second portions 504 and 506 that are configured and arranged for fluid communication with each other. In one embodiment, the portion 504 may define a substantially conical chamber 504a, and the portion 506 may define a substantially cylindrical chamber 506a. As disclosed in more detail below, the chamber 506a may serve as a dust collection chamber. In addition to the chambers 504a and 506a, the cleaning element 500 may include various inlets and outlets. Particularly, the cleaning element 500 may include a sample inlet 508 that communicates with chamber 504a. As well, the cleaning element 500 may include a dirty air outlet 510 that communicates with the chamber 506a. Finally, the cleaning element 500 may include a clean air conduit 512 having a first end in fluid communication with the chamber 504a, and having a second end that extends out of the body 502 and terminates in a clean air outlet 514. The clean air conduit 512 may be constructed of any of the materials disclosed herein, including plastic or metal.

In operation, a sample is pulled into the cleaning element 500 by a pump, such as those disclosed herein. The configuration of the chamber 504a imparts a rotational motion to the sample flow such that relatively heavy materials such as liquid water or dust, for example, move towards the wall of the chamber 504a and then drop down into the chamber 506a where they can eventually be discharged, or removed, from. The air that carried those materials exits the chamber 506a by way of the dirty air outlet 510. The relatively lighter, and cleaner air, that results from removal of the heavy materials, then flows through the clean air conduit 512 and exits the cleaning element 500 by way of the clean air outlet 514, and then proceeds to a sample cell (see, e.g., FIGS. 1-4, 5a and 5b).

With regard now to FIGS. 8a-8d, details are provided concerning another embodiment of a cleaning element, denoted at 600. The materials employed in the construction of the cleaning element 600 may be similar or identical to those used in the other embodiments disclosed herein. As well, the cleaning element 600 may be employed in any system, such as system 100 for example, that utilizes a cleaning element having a three port configuration. Examples of such systems are disclosed in FIGS. 1-4 and 5a-5b. In terms of its operation, the cleaning element 600 may operate in a similar fashion as the cleaning element 500, except that in the cleaning element 600, the rotational motion is imparted to the sample by chamber having a substantially cylindrical shape, rather than the substantially conical shape of the chamber 504a of the cleaning element 500. For example, the presence of the clean air conduit 608 in the chamber 602a may impart a rotational motion to the incoming sample stream.

In general, the cleaning element 600 may include a body 602 that may define a chamber 602a that may be substantially cylindrical. In addition to the chamber 602a, the cleaning element 600 may include various inlets and outlets. Particularly, the cleaning element 600 may include a sample inlet 604 that communicates with chamber 602a. As well, the cleaning element 600 may include a dirty air outlet 606 that communicates with the chamber 602a. Finally, the cleaning element 600 may include a clean air conduit 608 having a first end in fluid communication with the chamber 602a, and having a second end that extends out of the body 602 and terminates in a clean air outlet 610. The clean air conduit 608 may be constructed of any of the materials disclosed herein, including plastic or metal.

With reference, finally, to FIGS. 9a-9d, another example of a cleaning element, denoted at 700, is disclosed. In general, the cleaning element 700 may include a body 702 that may define a chamber 702a that may be substantially cylindrical. In addition to the chamber 702a, the cleaning element 700 may include various inlets and outlets. Particularly, the cleaning element 700 may include a sample inlet 704 that communicates with chamber 702a by way of a perforated conduit 706. The perforated conduit 706 may be implemented, for example, as tubing, or a screen. The number, size, configuration, orientation, and spacing of the perforations may be selected as desired. The perforations may or may not all have substantially the same size and configuration.

As well, the cleaning element 700 may include a dirty air outlet 708 that communicates with the chamber 702a by way of the perforated conduit 706. Finally, the cleaning element 700 may include a clean air outlet 710 in communication with the chamber 702a.

In operation, an incoming sample will have linear momentum as it travels through the conduit 706. A portion of the air sample changes direction as it is pulled laterally through the perforations of conduit 706 and then out through the clean air outlet 710. The heavier particles in the incoming sample will tend to travel in a straight line through to the end of the conduit 706 and out the dirty air outlet 708. In some embodiments, some or all of the perforated conduit 706 may be removable so as to facilitate cleaning of the chamber 702a and/or perforated conduit 706, and/or to permit repair or replacement of the perforated conduit 706. In some instances, the perforated conduit 706 may be replaced with another perforated element having a different configuration that is calculated to provide one or more desired effects with regard to an incoming sample.

F. Operational Aspects of an Example Embodiment of a Cleaning Element

With continued reference to the Figures, further details will now be provided concerning example operational aspects of some example embodiments. In particular, operation of the pump 102 may cause a gas sample to be drawn, from the atmosphere for example, into the cleaning element 400 by way of the inlet port 402. The pressure differential imparted by the pump 102 may be sufficiently large to draw the gas sample into the cleaning element 400 at a relatively high speed, such as about 10 m/s to about 150 m/s, for example.

As a consequence of the conical configuration of the chamber 408, and the tangential arrangement of the inlet port 402 relative to the chamber 408, a vortex flow may be imparted to the incoming gas stream, in which at least a portion of the gas flow rotates about a longitudinal axis defined by the chamber 408. Centrifugal, buoyancy, inertial and/or gravitational effects may cause relatively heavier materials, such as liquids and solids for example, in the rotating gas stream to be separated from the gas in the gas stream and deposited on the walls of the chamber 408 and/or collected proximate the bottom or narrow end of the chamber 408. Such liquids and solids may include, for example, dirt, dust and/or water droplets, and example gases that may be present in an incoming gas stream include water vapor, carbon dioxide, and atmospheric air.

Where the cleaning element 400 is a two port device, separated materials may be collected at the bottom of the chamber 408 for subsequent removal. If the cleaning element 400 includes a dirty gas outlet port 406, the separated materials may be directed to an external collection unit and/or to a location downstream of the sample cell 104 but upstream of the pump 102.

The separation of various materials from the incoming gas stream may result in a relatively cleaner flow of gas that exits the cleaning element 400 through the clean gas outlet 404. It should be noted that "clean" gas is a relative term that may embrace gas flows substantially free of foreign materials such as dirt, dust, and water vapor, but also more generally embraces any flow of gas that is relatively cleaner than the sample that was drawn into the cleaning element 400. The momentum of the solid and or liquid particles keeps them from moving towards the center of rotation. Further, the rotational motion of the gas in the chamber 408 may result in a pressure differential that tends to push heavier-than-air particles away from the center of rotation. Thus air drawn from the center of the vortex is relatively clean, and also may be relatively less dense than the sample gas inasmuch as various materials may have been separated from the sample gas to produce the clean gas.

Particularly, the clean gas then flows out the clean gas outlet port 404 of the cleaning element 400 through the sample tube 108 to the sample cell 104 where it can be analyzed. Because the gas is relatively clean, build-up of dirt and other materials in the sample cell 104 may occur relatively more slowly than would otherwise be the case. Thus, the sample cell 104 may remain within acceptable operational parameters a relatively longer time, thereby reducing the maintenance costs and burdens associated with the system 100.

As well, because separated materials may not be retained in the cleaning element 400 itself, the frequency response associated with the system 100 may remain in an acceptable range relatively longer than if separated materials were permitted to accumulate in the cleaning element 400.

G. Variations Applicable to Embodiments of the Invention

Embodiments of the cleaning elements disclosed herein may additionally, or alternatively, incorporate one or more of the variations set forth below.

As noted herein, embodiments of the cleaning element may use a vortex or other means to separate relatively high mass particles. To this end, a cleaning element may include, for example, an elbow or other shaped passage to induce rapid changes in flow direction, directed flow onto a flat or contoured surface to catch material, or straight flow through a perforated tube to let cleaner air out the sides.

As another example, embodiments of the cleaning element may be configured to accumulate removed material, pull the removed material away continuously or discontinuously, using the sample pump or other means, such as a second pump for example.

As well, a cleaning element and/or related system may include a self-cleaning mechanism, based on reversing the pump flow or pushing flow with a second pump or a source of compressed gas. Such functionality may be achieved by way of passive devices such as check valves, or active devices such as solenoid valves.

Finally, a cleaning element may be heated, either continuously or in some other fashion, in order facilitate a reduction in the attenuation of the sticky gas fluctuations discussed elsewhere herein.

H. Example Method

Figure 10:
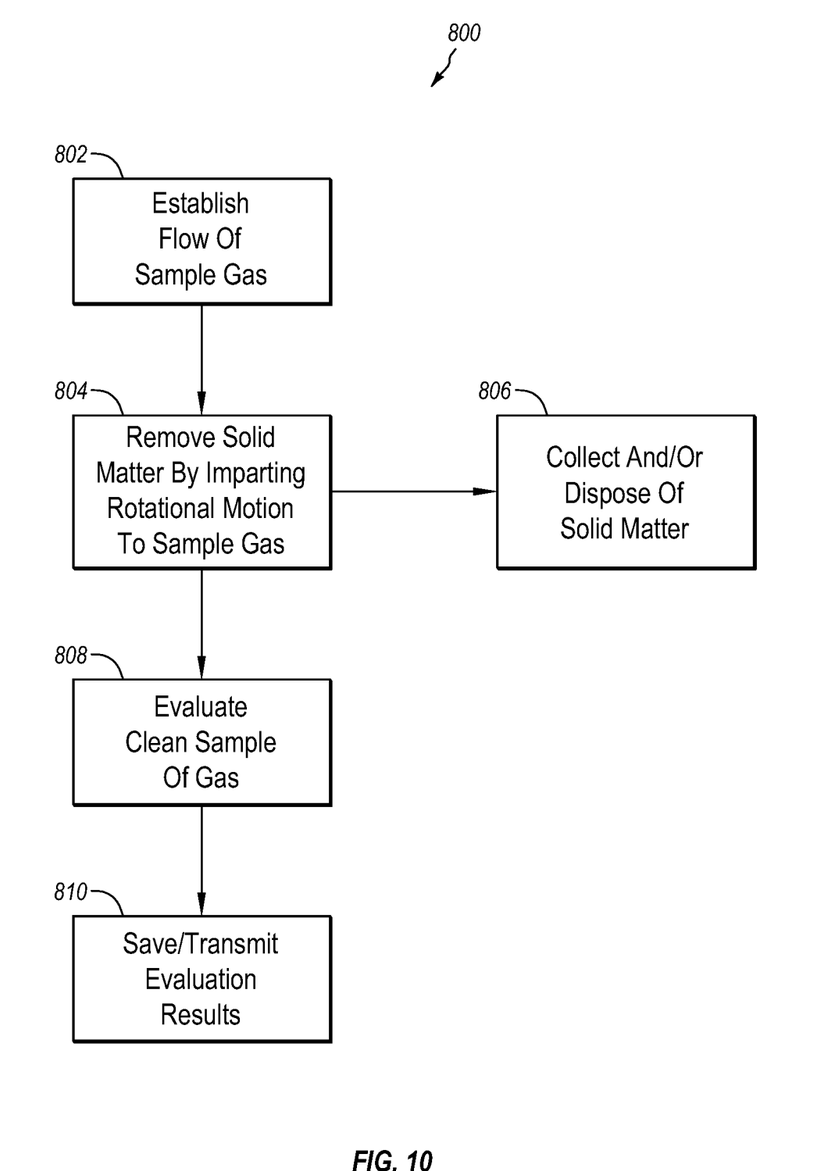
FIG. 10 is a flow diagram of an example method.

With attention now to FIG. 10, details are provided concerning an example method 800. The method 800 commences at 802 where a flow of a sample stream of gas is established. The flow of the sample stream of gas may be established, for example, through the use of a component such as the pump disclosed herein. In some instances, the sample stream of gas is taken from the environment of the earth, although the sample stream of gas may be taken from other environments instead. The gas sample may include solid material, examples of which are disclosed herein and may include liquid water and dust. As well, various types and combinations of gases, such as the gases disclosed herein, may be constituents of the gas stream. The flow of the sample stream of gas may be produced as the result of a single sampling process, or may result from the cumulative effect of several sampling processes. The sampling may be conducted randomly, or on some type of regular basis.

At 804 of the method 800, at least some solid matter is removed from the sample stream of gas by imparting a rotational motion to the sample gas. In general, the rotational motion may cause the solid matter to collect 806 at one or more designated locations. This rotational motion may be imparted, for example, by embodiments of the cleaning element disclosed herein. Additionally, or alternatively, the solid matter may be discharged as a component of a dirty gas stream. In any case, removal 806 of the solid matter may result in a stream of gas that is relatively cleaner than the initial sample. The clean stream of gas may be sufficiently free of solid matter that it can be analyzed and evaluated.

Once a clean sample of gas has been produced, the method 800 moves to 808 where the clean sample of gas is subjected to one or more analysis and evaluation processes. In one particular example, which is not limiting of the invention, the clean sample of gas is subjected to an optically-based analysis, such as may be performed in connection with an optical sample cell such as is disclosed herein. In one particular example, the optically-based analysis may include directing light into the sample of the clean stream of gas, and then measuring the influence of the sample of the clean stream of gas on the light. However, any other process(es), which may or may not be optically-based, that provide insight into the constituents and other characteristics of the clean sample may additionally, or alternatively, be employed.

In one example, the optically-based analysis may comprise an element of, or otherwise be employed in connection with, an eddy covariance measurement and analysis. More particularly, an eddy covariance measurement and analysis process may include, as one element, optically-based evaluation and analysis of a sample gas. Performance of the eddy covariance measurement and analysis process may produce data that enables conclusions to be drawn concerning the flux of a particular constituent of a gas sample, where one example constituent is water vapor and an associated gas sample is atmospheric air. Other example constituents and gas types are disclosed elsewhere herein.

I. Functional Elements

It will be apparent from the present disclosure that embodiments of the cleaning element comprise example structural implementations of a means for separating a first constituent from a flow of gas entering a sample gas analyzer by inducing vortex flow in the flow of gas and/or a means for separating a first constituent from a flow of gas entering a sample gas analyzer by inducing a change in direction of the flow of gas. Any other structural element(s), and combinations thereof, operable to implement functionality comparable to one or more of the aspects of the functionality disclosed herein are likewise considered to fall within the scope of this disclosure and example embodiments of the invention. The scope of the invention is, accordingly, not limited to the example structural implementations disclosed herein.

J. Example Computing Devices and Environments

The embodiments described herein may include the use of a special purpose or general-purpose computer, including data loggers and analyzers for example, which may include various computer hardware or software modules, as discussed in greater detail below.

Embodiments within the scope of the present invention may also include computer-readable media for carrying or having computer-executable instructions or data structures stored thereon. Such computer-readable media can be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium which can be used to carry or store desired program code means in the form of computer-executable instructions or data structures and which can be accessed by a general purpose or special purpose computer. When information is transferred or provided over a network or another communications connection (either hardwired, wireless, or a combination of hardwired or wireless) to a computer, the reader properly views the connection as a computer-readable medium. Thus, any such connection is properly termed a computer-readable medium. Combinations of the above should also be included within the scope of computer-readable media.

Computer-executable instructions comprise, for example, instructions and data which cause a general purpose computer, special purpose computer, or special purpose processing device to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used herein, the term "module" or "component" can refer to software objects or routines that execute on the computing system. The different components, modules, engines, and services described herein may be implemented as objects or processes that execute on the computing system (e.g., as separate threads). While the system and methods described herein are preferably implemented in software, implementations in hardware or a combination of software and hardware are also possible and contemplated. In this description, a "computing entity" may be any computing system as previously defined herein, or any module or combination of modulates running on a computing system.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A sample gas analyzer, comprising:
   a sample cell configured to receive a gas sample;
   a sample tube having a body defining a passageway that is in communication with the sample cell, and the body including an intake portion; and
   a cleaning element disposed upstream of the sample cell, the cleaning element comprising:
      a body having a chamber configured to aid in imparting a rotational motion to a fluid stream entering the chamber;
      an inlet port in communication with the chamber and configured and arranged for communication with the atmosphere; and
      an outlet port in communication with the chamber and the sample cell.

2. The sample gas analyzer as recited in claim 1, wherein the inlet port defines an axis that is generally tangential to a portion of the chamber.

3. The sample gas analyzer as recited in claim 1, wherein the inlet and outlet ports are located proximate a first end of the chamber.

4. The sample gas analyzer as recited in claim 1, wherein the outlet port is generally coaxial with a longitudinal axis defined by the chamber.

5. The sample gas analyzer as recited in claim 1, wherein the chamber is generally conical or generally cylindrical in shape.

6. The sample gas analyzer as recited in claim 1, wherein the cleaning element comprises an additional outlet port in communication with the chamber.

7. The sample gas analyzer as recited in claim 6, wherein the outlet port comprises a clean gas outlet port, and the additional outlet port comprises a dirty gas outlet port.

8. The sample gas analyzer as recited in claim 1, wherein the sample gas analyzer comprises a closed-path configuration configured to capture a gas sample.

9. The sample gas analyzer as recited in claim 1, wherein the cleaning element is operable to separate a liquid from the flow of gas.

10. The sample gas analyzer as recited in claim 1, wherein the cleaning element is operable to separate a solid from the flow of gas.

11. The sample gas analyzer as recited in claim 1, wherein the cleaning element is operable to separate one or more of solids and liquids from the flow of gas, wherein the flow of gas includes one or more of carbon dioxide ($CO_2$), methane, nitrous oxides, ammonia and water vapor.

12. The sample gas analyzer as recited in claim 1, wherein the cleaning element is operable to substantially prevent one or both of a solid and a liquid from reaching one or more of a wall of the sample cell, a window of the sample cell, and a wetted surface associated with the sample cell.

13. The sample gas analyzer as recited in claim 1, wherein the cleaning element comprises a cyclone separator in communication with the sample tube.

14. The sample gas analyzer as recited in claim 1, wherein the outlet port is a dirty gas outlet port that is in fluid communication with a filter and an orifice.

15. The sample gas analyzer as recited in claim 1, wherein the outlet port is a dirty gas outlet port that is in fluid communication with an outlet of the sample cell, and the outlet of the sample cell and the dirty gas outlet port are both in fluid communication with a pump inlet.

16. The sample gas analyzer as recited in claim 1, wherein the outlet port is a dirty gas outlet port that is in fluid communication with a pump inlet.

17. The sample gas analyzer as recited in claim 1, wherein an outlet of the sample cell is in fluid communication with a pump inlet.

* * * * *